United States Patent
Van Vugt et al.

(10) Patent No.: US 9,993,193 B2
(45) Date of Patent: Jun. 12, 2018

(54) DETECTION OF BREATHING IN THE BEDROOM

(75) Inventors: Henriette Christine Van Vugt, Utrecht (NL); Rene Martinus Maria Derkx, Eindhoven (NL); Adrienne Heinrich, Den Bosch (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 914 days.

(21) Appl. No.: 13/976,225

(22) PCT Filed: Jan. 10, 2012

(86) PCT No.: PCT/IB2012/050108
§ 371 (c)(1),
(2), (4) Date: Jun. 26, 2013

(87) PCT Pub. No.: WO2012/095783
PCT Pub. Date: Jul. 19, 2012

(65) Prior Publication Data
US 2013/0289432 A1    Oct. 31, 2013

(30) Foreign Application Priority Data
Jan. 12, 2011   (EP) ...................................... 11305029

(51) Int. Cl.
*A61B 5/08*         (2006.01)
*A61B 5/00*         (2006.01)
(Continued)

(52) U.S. Cl.
CPC .......... *A61B 5/4809* (2013.01); *A61B 5/0077* (2013.01); *A61B 5/0803* (2013.01);
(Continued)

(58) Field of Classification Search
None
See application file for complete search history.

(56) References Cited

U.S. PATENT DOCUMENTS

| 5,197,490 A |   | 3/1993 | Steiner et al. |
| 5,797,852 A | * | 8/1998 | Karakasoglu ........ A61B 5/7475 600/529 |

(Continued)

FOREIGN PATENT DOCUMENTS

| DE | 202004033907 A1 | 2/2006 |
| WO | 2008145952 A1 | 12/2008 |

OTHER PUBLICATIONS

Qi, Yue, Guo-Chang Huang, and Yun-Hong Wang. "Carrying object detection and tracking based on body main axis." 2007. Wavelet Analysis and Pattern Recognition, 2007. ICWAPR'07. International Conference on. vol. 3. IEEE.*

(Continued)

*Primary Examiner* — Jacqueline Cheng
*Assistant Examiner* — Jairo Portillo

(57) ABSTRACT

A method and a system for unobtrusively measuring a person's respiration, wherein at least two microphones positioned at either side of a person's head are utilized based on a distance of the persons head to the microphones and an identification of which microphone is in a line of sight and which is out of the line of site of the person's breathing as computed on the basis of images captured by a video camera.

12 Claims, 2 Drawing Sheets

(51) Int. Cl.
*A61B 5/11* (2006.01)
*A61B 7/00* (2006.01)

(52) U.S. Cl.
CPC .......... *A61B 5/0816* (2013.01); *A61B 5/1116* (2013.01); *A61B 5/4806* (2013.01); *A61B 7/003* (2013.01); *A61B 5/4818* (2013.01); *A61B 5/6891* (2013.01)

(56) References Cited

U.S. PATENT DOCUMENTS

| | | | | |
|---|---|---|---|---|
| 6,430,295 | B1* | 8/2002 | Handel | G10K 11/345 381/71.11 |
| 6,758,819 | B2* | 7/2004 | Nomura | A61B 5/0285 600/481 |
| 7,035,432 | B2* | 4/2006 | Szuba | A61B 5/1128 382/103 |
| 2002/0090094 | A1* | 7/2002 | Amir | H04R 3/00 381/92 |
| 2004/0234080 | A1* | 11/2004 | Hernandez | G10K 11/178 381/71.11 |
| 2005/0136848 | A1* | 6/2005 | Murray | G10L 21/0208 455/79 |
| 2006/0204026 | A1* | 9/2006 | Kargus | H04R 1/086 381/359 |
| 2007/0293781 | A1* | 12/2007 | Sims | A61B 5/1135 600/534 |
| 2008/0146289 | A1* | 6/2008 | Korneluk | H04M 1/6041 455/569.1 |
| 2008/0312516 | A1 | 12/2008 | Ozaki et al. | |
| 2008/0312918 | A1* | 12/2008 | Kim | G10L 15/01 704/233 |
| 2009/0177327 | A1 | 7/2009 | Turner et al. | |

OTHER PUBLICATIONS

NPL English Translation of DE 10 2004 033 907.*
F Series, I Marc, "Changes in snoring characteristics after 30 days of nasal continuous positive airway pressure in with non-apnoeic snoring: a controlled trial", Thorax 1994, 49, pp. 562-566.
Kaveh Malakuti, "Towards an Intelligent Bed Sensor: Non-intrusive Monitoring of Sleep Disturbances via Computer Vision Techniques", A Thesis Submitted in Partial Fulfillment of the Requirements for the Degree of Master of Applied Science in the Depart. of Electrical and Computer Engineering, pps. 1-93, DOI 10.1378/chest. 103.6.1769.
I. Marc and L. Atton, "Comparison of snoring measured at home and during polysomnographic studies", CHEST, American College of Chest Physicians, U.S. vol. 103, No. 6, Jun. 1, 1993, pp. 1769-1773.
Viola, Paul et al Rapid Object Detection using a Boosted Cascade of Simple Features, Accepted Conference on Computer Vision and Pattern Recognition 2001.
"Sleep Study Questions and Answers: A Guide for Patients", Canadian Sleep Society, 2006.
Gritti, Tommaso "Toward Fully Automated Face Pose Estimation" IMCE'09, Oct. 23, 2009.
Derkx, Rene "Adaptive Azimuthal Null-Steering for a First-order Microphone Response" International Workshop on Acoustic Echo and Noise Control, 2010.
De Haan, Gerard et al "True-Motion Estimation with 3-D Recursive Search Block Matching", IEEE Transactions on Circuits and Systems for Video Tecnology, Nol. 3, No. 5, Oct. 1993.

* cited by examiner

# DETECTION OF BREATHING IN THE BEDROOM

FIELD OF THE INVENTION

The invention relates to the field of unobtrusively detecting respiration.

BACKGROUND OF THE INVENTION

Respiration is an important parameter that gives an indication of the physiological state of a person, e.g., whether the person is in a relaxed state or sleeping. Sleep and relaxation parameters such as respiration can be measured in different ways, and sleep laboratories often make use of obtrusive sensors such as EEG/PSG or other on-body sensors such as respiratory belts. Unobtrusive measuring of sleep parameters is more convenient for the sleeper, and unobtrusive measuring is preferred over existing obtrusive measurement techniques for home, medical and lifestyle solutions.

A living body information detection and display method is disclosed in US 2008/0312516 A1, together with a sleeping posture and position apparatus. This is used to correctly and suitably capture an abnormal condition in a living body while the living body is sleeping/lying on a bed or on the apparatus. Living body information and sleeping posture/position are captured by pressure sensors placed under a sleeper. The living body information may include, for example, respiratory information, body movement information, and sleeping posture.

Malakuti, K. reports a data acquisition system for monitoring sleep, wherein said data acquisition system uses 144 pressure sensors embedded in a bed sheet (Intelligent Bed Sensor) for measuring the pressure that the patient's body exerts on the bed. A video camera and a microphone recorded additional information to be used for evaluating the Intelligent Bed Sensor and are not part of the data acquisition system (Malakuti, I. Towards an Intelligent Bed Sensor: Non-intrusive Monitoring of Sleep Disturbances via Computer Vision Techniques; 2008, Thesis, University of Victoria).

To detect respiration unobtrusively, a set of small microphones can be used that can be positioned on the side of a person's bed, close to the persons's head. For example, Sériè, F. and Marc, I. reported recording of snoring by two microphones which were placed symmetrically on each side of a bed, 70 cm above the bed surface and 85 cm apart, and angled to point directly toward the centre of the bed at the normal head position. The signal was preamplified, mixed, equalised and analysed with a spectrum analyser to get the snoring sound pressure level. To take into account the acoustic characteristics of the recording system, a calibration of the sound signal preceded the sleep studies. The sensitivity of the equaliser was adjusted to give a Pink Noise an intensity of 77 dB SPL. Following this procedure the equalised signal of the breathing noise was analysed by the spectrum analyser and transferred to a computer for interpretation (Sériè, F. and Marc, I., Thorax 1994; 49:562-566).

However, breathing produces a relatively weak sound signal compared to snoring. Moreover, other sounds than just breathing may be present in a bedroom or relaxation area, e.g., from ventilation, from movements of the person him/herself, noises or breathing of another person, and the like. These other sounds can be regarded as noise that is detected on top of the "desired" respiration signal, and renders measuring and analysis of the breathing more difficult.

Using two microphones at the same time, wherein said microphones are arranged on opposite sides of the person's head, may be useful for proper detection of the person's respiration. For example, the two signals from said microphones may be combined. However, this method may be improved upon by taking into account information on the person's head position.

SUMMARY OF THE INVENTION

It is a first object of the invention to provide a system for unobtrusively measuring a person's respiration.

It is a further object of the invention to provide a method for unobtrusively measuring a person's respiration.

The first object is achieved by a system comprising at least two microphones, at least one video camera, an infrared light source for illumination in the dark, offering the possibility to project an infrared pattern, wherein said at least two microphones are operatively linked to said at least one camera. The camera and illumination source can be integrated in one casing. Said at least two microphones are positioned on either side of the person's bed close to the person's head position to measure the respiration of said person. Said camera is positioned to capture images indicating the relative position of the person's head to the at least two microphones. The images captured by the camera permits estimation of the exact position of the person like if he is lying on his back (supine position), in a lateral position on either the right side or the left side, or on the belly (prone position) by analyzing the light reflected from said person or the blanket. Analyzing of the images may also allow distinguishing whether more than one person is in the bed so as to identify the target person.

In a preferred embodiment of the invention, said at least two microphones are steerable. Preferably, said at least two microphones are mechanically and/or electronically steerable. Steerability of the at least two microphones permits to improve signal-to-noise ratio when respiration of the person is measured, in particular when respiration is measured in the presence of noise point-sources.

In another or additional preferred embodiment of the invention, the at least one camera or an additional camera is positioned above the height of the bed surface, preferably shifted beyond the foot end of the bed. This position of a camera is superior for capturing the light reflected from the person lying in bed or from the blanket said person may be covered with. This position of the camera is preferred for determining whether the person is lying in either supine or prone position, or in lateral position to its right or left side and to indicate the distance between the head and the microphones.

In another or additional preferred embodiment, the at least one camera is positioned at the foot end or side of the bed, close to the corner of the bed between the foot end and the side of the bed where the sleeping person is located, above the height of the bed surface. This position of the camera permits better motion analysis of the whole body of the person, and in particular, extraction of the last top movement of the body's main axis.

In a preferred embodiment of the invention, the system further comprises a digital signalling processor and/or an adaptive filter for providing an enhanced and/or improved signal output of the signals received from the at least two microphones and provided from said at least two microphones to said digital signalling processor or adaptive filter.

It is a further object of the invention to provide a method for unobtrusive measuring a person's respiration.

Said further object is achieved by a method wherein images of a person lying down or lying in bed are captured by at least one video camera and are analysed to indicate where the person's head is positioned relative to at least two microphones which are positioned on either side of the person's bed and/or to indicate whether said person is lying in supine position, prone position or lateral position to its left or right side. The method further comprises computing the distance of the person's head to said at least two microphones, and to use said distances as parameters in audio analysis of signals obtained from at least one of said at least two microphones.

In a preferred embodiment of the invention, the images captured by said at least one camera are analyzed for motion of the whole body of said person, in determining the main body axis of the body of said person, and in extracting the last top movement of the main body axis. This motion analysis of the whole body of said person permits to precisely indicate where the person's head is positioned relative to the at least two microphones, and to compute the distance of the person's head to each of said at least two microphones such that the at least two microphones may be steered for improving the breathing to be measured and/or to improve the signal-to-noise ratio.

In another preferred or additional embodiment of the invention, the images are analyzed for the distribution and/or pattern of the light reflected from the person or from a blanket covering said person, and the position is determined that said person is laying in. This analysis permits to determine the microphone of said at least two microphones which is in the line-of-sight of the breathing person.

In a preferred embodiment of the invention, the computed distances of the person's head to the at least two microphones are used for steering at least one of said at least two microphones. The steering of at least one of the microphones improves recording of the desired breathing over noise, because the microphone in the line-of-sight of the breathing may be steered towards the person's head and/or the other microphone(s) may be steered away from a noise source thereby improving the signal-to-noise ratio. Preferably, the microphones are steered mechanically and/or electronically.

In a further preferred embodiment of the invention, the signals from the at least two microphones are processed in a digital signalling processor leading to an enhanced and/or improved signal output from the digital signalling processor for further analysis.

In a further preferred embodiment of the invention, the signals from the at least two microphones undergo adaptive filtering wherein the signal from the microphone out of the line-of-sight of the person's breathing is used to estimate the noise in the microphone in the line-of-sight of the persons's breathing where said estimate of the noise is subtracted from the signal of the microphone in the line-of-sight of the person's breathing, said adaptive filtering leading to an enhanced signal output from the adaptive filter for further analysis.

DETAILED DESCRIPTION OF EMBODIMENTS

Figure 1:
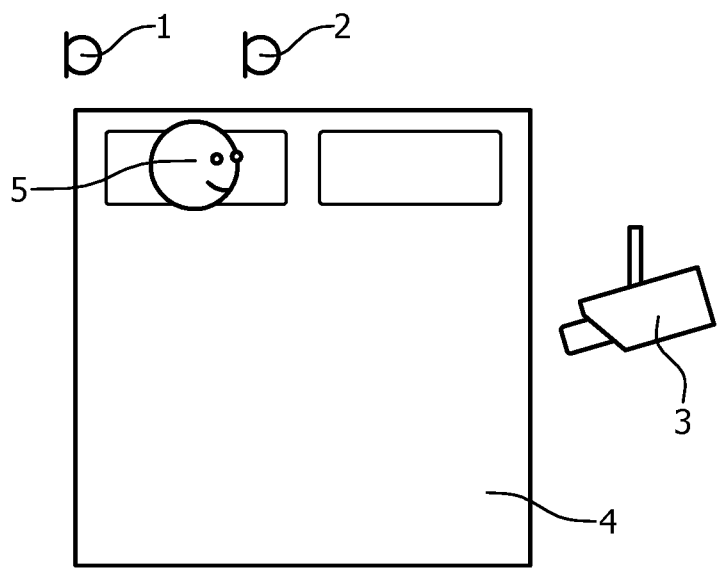
FIG. 1 depicts the general set up of the system.

The present invention will be described with respect to particular embodiments and with reference to the figures, but the invention is not limited thereto, but only to the claims. The drawings described are only schematic and are non-limiting. In the drawings, the size of some of the elements may be exaggerated and not drawn on scale for illustrative purposes.

Where an indefinite or definite article is used when referring to a singular noun, e.g. "a", "an", "the", this includes a plural of that noun unless something else is specifically stated. Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein. Moreover, the terms top, bottom, over, under, beyond and the like in the description and in the claims are used for descriptive purposes and not necessarily for describing relative positions. It is to be understood that the terms so used are interchangeable under appropriate circumstances and that the embodiments of the invention described herein are capable of operation in other orientations than described or illustrated herein. It is to be noted that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

FIG. 1 depicts the general set up of the system pursuant to the present invention. The system comprises at least two microphones 1, 2 and at least one video camera with integrated infrared illumination with the possibility to illuminate the sleeping person with a pattern 3. Said at least two microphones 1, 2 are positioned on either side of the person's bed 4 close to the person's head position 5.

The video camera takes images of the resting or sleeping person. The images taken by the camera may precisely indicate where the persons's head is positioned relative to the at least two microphones. In addition, the images taken by the camera permit estimation if the person is lying sideways on its left side or on its right side, or in either supine or prone position, in that the distribution of the reflected light is analysed. A more detailed spatial analysis of the higher and lower reflected light intensities may give a first indication if the person is lying on its left or on its right side, i.e. facing the left microphone or the right microphone. The side said person is lying on affects the strength of the signal in the two microphones, e.g. the signal of the left microphone is stronger than the signal in the right microphone when a person is breathing to the left direction, and vice versa. More generally speaking, the microphone proximal to the person's head receives a stronger breathing signal than the microphone being distal to the person's head.

Also, if two persons are relaxing or sleeping in the same bed, camera images taken can indicate to where the persons and their heads are positioned. The position of the "target" person, i.e. the person who's respiration is to be monitored, and the other person, the so-called "noise" person, can be taken into account to detect the breathing of the "target" person by analyzing the movements of said two persons. Every time a person moves his/her head, the position of the head with respect to the two microphones is updated.

According to a first embodiment of the system, the camera images may indicate precisely where the person's head is positioned relative to the at least two microphones. The camera may thus be used as an off-body sleep monitoring device for video-based actigraphy. Motion detection and motion estimation is performed on consecutive images where highlighted motion areas are returned. Based thereon, orientation of the sleeping person may be extracted, and the location of the persons's head. The body parts are segmented by dividing the main axis of the body based on general body proportions. When the head touches the pillow, i.e. the last movement of the head part, the location of the image is logged and the position of the head with respect to the two microphones is given to the audio analysis module. The video process for computing the distance between the head and the microphones is outlined in FIG. 2. When the head is moving throughout the night, the computed motion vectors are analyzed and an updated head position and orientation are given to the audio analysis.

Figure 2:
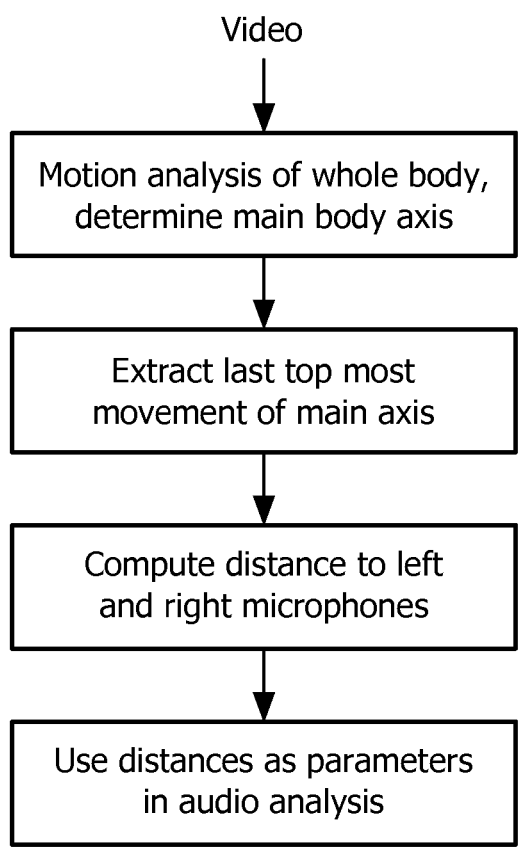
FIG. 2 outlines the video process for computing distance between head and microphones.

FIG. 2 shows that the motion analysis of the whole body of a person is used to determine the main body axis of the person. This is determined by analysing consecutive images captured by the video camera. The last top most movements of the main body axis are extracted, and the distance to the left microphone and to the right microphone is computed. The computed distances are then used as parameters in audio analysis of the person's breathing.

Figure 3:
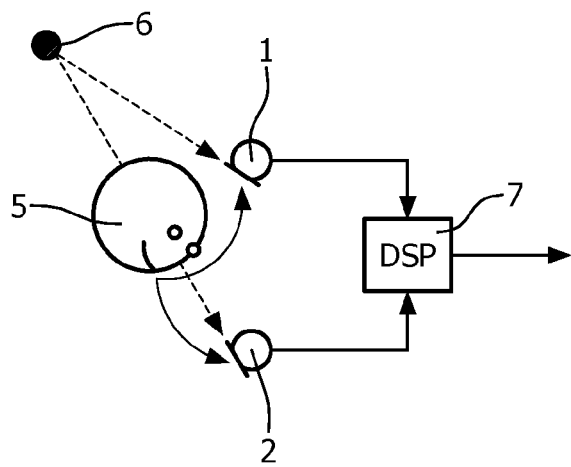
FIG. 3 illustrates an embodiment comprising steering of a spatial notch towards a point-source of noise.

After knowing the location of the head with respect to the at least two microphones, the signal-to-noise ratio of the two microphones may be improved by steering the directional-pattern of the microphones towards the person asleep. This steering can be done either mechanically or electronically. Also such a microphone-array can place a spatial notch toward a noise point source. FIG. 3 illustrates an example, wherein a fan is present as noise point-source 6 in the room, a spatial notch can be—electronically—steered toward this point source 6. For example, the diaphragm of the directional microphone 1 (e.g. a dipole microphone with a figure-of-eight beampattern) is steered perpendicular to the noise point-source 6. In this way, the response of the microphones 1, 2 with respect to the noise point-source 6 is minimized, and the signal-to-noise ratio is improved. The signals obtained from the microphones 1, 2 are processed in a digital signalling processor 7 providing an enhanced signal output.

According to another and/or additional embodiment, the images taken by the camera may indicate to what side the person is breathing. Based on the distribution of the light reflected from the person in bed or from the blanket said person may lay underneath, it may be determined whether said person is lying sideways, or in either supine or prone position. When it is determined that the person is lying sideways, a more detailed analysis of the reflected light intensity pattern may be performed, and based on the orientation of the legs of said person, the side the person is facing to and thus the orientation of the person's head is derived. The reflected light in the leg area has a higher intensity than the non-body area. This difference in light intensity allows determining the side said person is facing to. Particularly, the angle and orientation of the legs are indicative factors for estimating the left or right side orientation. When a person is lying flat, face and head pose detection can be applied to estimate the angle of the face. Additionally, motion vectors which may be computed indicate the motion of the head, and may be used to estimate orientation the person's face. The video respiration analysis may be used in combination with the audio analysis to improve the audio signal analysis.

Figure 4:
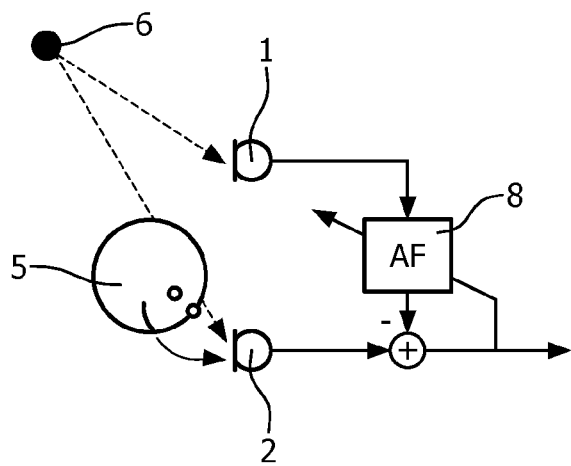
FIG. 4 illustrates an embodiment comprising an adaptive filtering technique to improve signal-to-noise ratio.

Knowing the orientation of the head of the person with respect to the microphones is very helpful when the breathing of the person is very soft. In such instances, as illustrated in FIG. 4, a signal-to-noise ratio may be enhanced and/or improved. For this, the single microphone 2 which is in the "line-of-sight" of the breathing person is used as so-called "primary" microphone. The other microphone 1 is used as a noise reference microphone. Adaptive filtering techniques may be used to improve the signal-to-noise ratio.

The noise of noise point-source 6 is picked up by both microphones 1,2 while breathing of the person is mainly picked up by primary microphone 2. The adaptive filter 8 (AF) is adapted in such away that it produces an estimate of the noise in the primary microphone 2. By subtracting this estimated noise signal from the primary microphone signal, an enhanced output signal is produced where the noise of the noise point-source is ideally not present anymore.

According to another and/or additional embodiment, the images taken by the camera may indicate to where the two people and their heads are positioned when two persons are in the same bed, and both are breathing. One person can be considered the "target" person whose respiration should be measured, and the other person is referred to as the "noise" person as for the breathing analysis. The two video analysis approaches sketched above to determine the location and orientation of the head of the sleeping person can be extended to the shared bed situation when two persons sleep in one bed. The image is divided and the two parts processed independently. Due to spatial concentration of the motion output per person and based on the assumption that the two persons do not sleep such that the two heads are touching each other, the two persons can be easily segmented for the video analysis.

After the analysis of the video has taken place and the location and orientation of both heads of the persons asleep are known, microphone signals can be processed in such a way that the influence of the bed partner is minimized in the breathing signal. A way to do this is by using the steered microphone technique as mentioned before. However, it might be the case that the bed-partner is very close to one of the two microphones, and the breathing of the bed-partner cannot be seen as a point-source any more.

Figure 5:
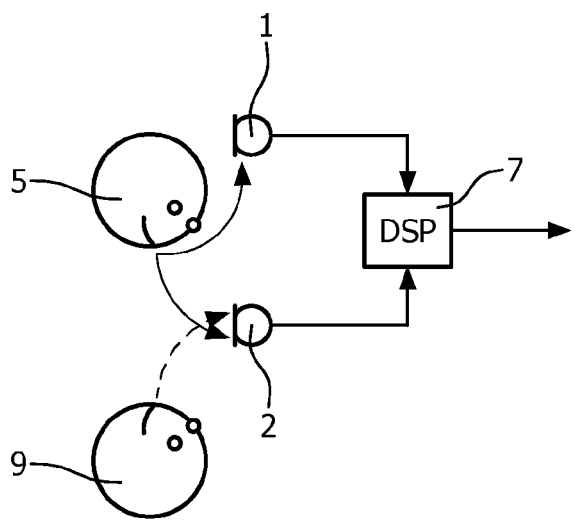
FIG. 5 illustrates a situation wherein the heads of two persons are very close to at least one microphone.

As can be seen in FIG. 5, the breathing of the bed-partner 9 is picked up by right microphone 2, while the desired breathing is picked up by both (left and right) microphones 1, 2. It can not be made use of the adaptive filter technique as the desired breathing is picked up by both microphones and a clean noise reference can not be constructed. In such a case only the left microphone 1 is used for capturing the breathing of the desired breathing signal and excludes the signal from right microphone.

The invention is useful to make reliable applications in which proper measurement of breathing in the bedroom is important. Such application may for example be paced breathing systems, sleep coaching, systems for sleep analy-

The invention claimed is:

1. A method of operating a system for unobtrusively measuring a person's respiration, the method comprising acts of:
   capturing images of a person lying down or lying in bed, by at least one video camera,
   analyzing the images, to determine the rotation of the head of the person about the longitudinal axis of a body of the person,
   determining by the video processor, from the images and rotation of the head which of at least two microphones is a microphone in a line-of-sight of the person's breathing and which of the at least two microphones is a microphone not in the line-of-sight of the person's breathing,
   computing from the images by the video processor, a distance from the person's head to each of the at least two microphones positioned on opposite sides of the person's head, and
   measuring by an audio analyzer, the person's respiration depending on the distances from the head to each microphone computed by the video processor and on the determination by the video processor of which of the at least two microphones is the microphone in the line-of-sight and which of the at least two microphones is the microphone not in the line-of-sight, as parameters.

2. The method according to claim 1, comprising acts of analyzing the captured images for motion of a whole body of the person, determining a main body axis of the person, and extracting a last top movement of the main body axis.

3. The method according to claim 1, comprising acts of analyzing the images for a distribution and/or pattern of light reflected from a blanket covering the person, and determining a position the person is lying in.

4. The method according to claim 1, comprising an act of steering the at least two microphones using the parameters such that the microphone in the line-of-sight is steered towards the person's head and the microphone not in the line-of-sight is steered perpendicular to a noise source.

5. The method according to claim 4, wherein the at least two microphones are steered mechanically or electronically.

6. The method according to claim 1, comprising an act of processing signals from the at least two microphones using a digital signal processor leading to an enhanced signal output from the digital signal processor.

7. The method according to claim 1, comprising an act of adaptively filtering signals from the at least two microphones wherein a signal from the microphone out of the line-of-sight of the person's breathing is used to estimate noise in the microphone in the line-of-sight of the person's breathing wherein the noise is subtracted from the signal of the microphone in the line-of-sight of the person's breathing, the adaptive filtering leading to an enhanced signal output from the adaptive filter.

8. The method according to claim 1, wherein the act of analyzing the images comprises acts of determining when the person's head first touches a pillow on the bed, determining an orientation of the person's head relative to the at least two microphones and computing motion vectors to track the position and orientation of the persons head relative to the at least two microphones to provide an updated position and orientation of the person's head relative to the at least two microphones as the person moves.

9. The method according to claim 1, wherein the act of analyzing the images comprises an act of determining whether the person is lying in a supine position, a prone position, a lateral position facing left or a lateral position facing right.

10. The method according to claim 1, comprising an act of steering the at least two microphones using the parameters such that the microphone in line-of-sight is steered towards the person's head and the microphone not in line-of-sight is steered to place a spatial notch of the microphone towards a noise source.

11. A system for unobtrusively measuring a person's respiration, the system comprising:
    at least one video camera configured to capture images of a person lying down or lying in bed,
    at least two microphones positioned on opposite sides of the person's head,
    a video processor configured to analyze the images, to determine the rotation of a head of the person about the longitudinal axis of a body of the person,
    the video processor configured to determine from the rotation of the head and the images, which of the at least two microphones is a microphone in a line-of-sight of the person's breathing and which of the at least two microphones is a microphone not in the line-of-sight of the person's breathing,
    the video processor configure to compute a distance from the person's head to each of the at least two microphones positioned on opposite sides of the person's head, and
    an audio analyzer configured to measure the person's respiration depending on the distances from the head to each microphone computed by the video processor, and depending on the determination of which of the at least two microphones is the microphone in the line-of-sight and which of the at least two microphones is the microphone not in the line-of-sight, as parameters.

12. The system of claim 11, wherein the audio analyzer comprises one or more of: a digital signal processor and an adaptive filter.

* * * * *